United States Patent [19]
Kawajiri et al.

[11] Patent Number: 4,892,856
[45] Date of Patent: Jan. 9, 1990

[54] CATALYST FOR OXIDATION OF ACROLEIN AND PROCESS FOR PREPARATION THEREOF

[75] Inventors: Tatsuya Kawajiri; Shinichi Uchida, both of Himeji; Masahiro Wada, Nishinomiya, all of Japan

[73] Assignee: Nippon Shokubai Kagaku Kogyo Co., Ltd., Osaka, Japan

[21] Appl. No.: 201,026

[22] Filed: Jun. 1, 1988

[30] Foreign Application Priority Data

Jun. 5, 1987 [JP] Japan ................................. 62-139663

[51] Int. Cl.$^4$ .......................... B01J 23/22; B01J 23/28
[52] U.S. Cl. ..................................... 502/247; 502/306; 502/309; 502/312
[58] Field of Search ................. 502/312, 306, 309, 247

[56] References Cited

U.S. PATENT DOCUMENTS

| | | | |
|---|---|---|---|
| 4,138,366 | 2/1979 | Shaw et al. | 502/312 X |
| 4,259,211 | 3/1981 | Krabetz et al. | 502/312 X |
| 4,289,654 | 9/1981 | Bertolini et al. | 502/312 X |

Primary Examiner—W. J. Shine
Attorney, Agent, or Firm—Sherman and Shalloway

[57] ABSTRACT

A catalyst for use in the production of acrylic acid by catalytic gas phase oxidation of acrolein, comprising active substances represented by general formula

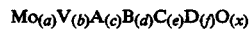

$Mo_{(a)}V_{(b)}A_{(c)}B_{(d)}C_{(e)}D_{(f)}O_{(x)}$ wherein Mo represents molybdenum, V represents vanadium, A represents at least one element selected from the group consisting of tungsten and niobium, B represents at least one element selected from the group consisting of iron, copper, bismuth, chromium, antimony, and thallium, C represents at least one element selected from the group consisting of alkali metals and alkaline earth metals, D represents at least one element selected from the group consisting of silicon, aluminum and titanium, and O represents oxygen; and further, a, b, c, d, e, f and x represent atomic ratios of Mo, V, A, B, C, D, and O respectively, and when $a=12$, then $b=2$ to 14, $c=0$ to 12, $d=0$ to 6, $e=0$ to 6 and $f=0$ to 30 and x is a numerical value determined depending upon the oxidation states of the other elements, and characterized by having a specific surface area of 0.50 to 15.0 m$^2$/g, a pore volume of 0.10 to 0.90 cc/g and a pore diameter distribution in which the pore diameters are distributed concentratedly in the ranges of from 0.1 to less than 1.0 μm, from 1.0 to less than 10.0 μm and from 10.0 to 100 μm. The catalyst can be prepared, with good reproducibility, by charging an unfired catalyst material powder composition into a centrifugal flow coating apparatus to form particles having an average diameter of 2 to 10 mm, and then firing the particles.

6 Claims, No Drawings

CATALYST FOR OXIDATION OF ACROLEIN AND PROCESS FOR PREPARATION THEREOF

This invention relates to a catalyst suitable for the production of acrylic acid from acrolein, which comprises molybdenum and vanadium as essential components, and a process for the preparation thereof. More specifically, this invention relates to a catalyst for the oxidation of acrolein, which has high activity and excellent durability and which is characterized by specific properties, and a process for the preparation of said catalyst with ease and good reproducibility.

There are many literature articles proposing various catalysts for producing acrylic acid at high yields by a catalytic gas phase oxidation reaction of acrolein. These proposals are mainly concerned with selection of components for catalysts and proportions thereof. Some of them are also concerned with selection of catalyst properties and production processes with reproducibility. Although there are not a few proposals concerning catalyst properties such as surface area, pore volume, etc., none of these proposed catalysts are found to be on a satisfactory level.

For example, as a disclosure of the surface area, it is described in Japanese Laid-Open Patent Publications Nos. 86812/1973 and 91010/1973 that the catalyst surface areas of 0.1 to 50 m$^2$/g are preferable. However, those catalysts described therein have defects of high reaction temperatures and low level of performance. Japanese Laid-Open Patent Publications Nos. 47276/1974 and 24183/1975 describe that the specific surface areas of 0.1 to 8 m$^2$/g are preferable. However, those catalysts described therein also have a defect of high reaction temperatures as high as about 300° C. With regard to the definition of the pore volume and surface area, it is described in Japanese Laid-Open Patent Publications Nos. 65395/1974 and 62409/1974 that the surface areas of 4 to 8 m$^2$/g and pore volumes of 0.1 to 0.2 ml/g are preferable. However, those catalysts described therein comprise cobalt and molybdenum as active components and they are technically on a low level.

Japanese Laid-Open Patent Publication No. 47590/1976 describes that a catalyst comprising phosphorus, molybdenum and thallium or an element of Group IA or II of the periodic table and formed by rolling particle-forming method so as to have a surface area of 4 to 20 m$^2$/g and a pore volume of 0.08 to 0.5 ml/g has reproduction in performance. However, this catalyst also has defects that the reaction temperature is high and the performance is unsatisfactory. Japanese Laid-Open Patent Publication No. 9737/1982 discloses a catalyst comprising, as essential components, molybdenum, vanadium, copper, iron, manganese, alkali earth metal or zinc, and oxygen and further including phosphorus as an optional component, and a process for the production of acrylic acid by using said catalyst in the oxidation of acrolein. And it discloses an embodiment of the catalyst in which an alundum having a diameter of 3.5 mm is allowed to carry catalyst components by a rotatory sugar coater. In the catalyst therein, the reaction temperature is relatively low, i.e., about 200° C., and said catalyst achieves a high level in the yields. However, the catalyst obtained by the process has a problem in respect of reproducibility of its properties.

The present inventors have had an idea that the catalyst properties are not determined by the mere definition of catalyst surface area and/or pore volume but that industrially-excellent catalysts can be obtained only when the catalysts are imparted with properties resulting from the combination of three factors of catalyst surface area, pore volume and pore diameter distribution. Meanwhile, in the case of carrying out the oxidation reaction of acrolein by the use of a reaction apparatus having a fixed bed or moving bed, catalysts are used, in general, in the form of pellets having a suitable size. Such pellets are formed by using a tablet-forming machine, extruder, pill-forming machine, rolling particle-forming machine, etc. However, the physical property of the resultant catalyst is not constant, that is, most cases show poor reproducibility of catalyst performance. Thus, in such forming methods, it is difficult to obtain catalysts without lowering the catalyst performance.

Therefore, the present inventors made assiduous studies to clear up those variations of catalyst performance which are caused at the time of forming catalysts by using various forming machines. As a result, it was found that in the case of a catalyst material containing Mo, V, A, B, C, D, and 0 (wherein Mo represents molybdenum, V represents vanadium, A represents at least one element selected from the group consisting of tungsten and niobium, B represents at least one element selected from the group consisting of iron, copper, bismuth, chromium, antimony and thallium, C represents at least one element selected from the group consisting of alkali metals and alkaline earth metals, D represents at least one element selected from the group consisting of silicon, aluminum and titanium, and O represents oxygen,) as active components, the catalyst performance lowers to a great extent and the performance and physical property vary depending upon forming methods, and it was also found that the main cause of the foregoing is that since the pores of the catalyst are conditioned at the formation time, the catalyst surface area, pore volume and pore diameter are controlled.

Accordingly, further studies were made with regard to the surface area, pore volume and pore distribution in order to obtain a catalyst comprising the above components and having excellent performance. As a result, it was found that such a catalyst has to satisfy three conditions that it has a surface area of 0.50 to 15.0 m$^2$/g, that it has a pore volume of 0.10 to 0.90 cc/g and that it has a pore diameter distribution in which the pore diameters are distributed concentratedly in the ranges of from 0.1 to less than 1.0 μm, from 1.0 to less than 10.0 μm and from 10 to 100 μm. The pore volume composed of pores having pore diameters in the range of from 10 to less than 100 μm is not less than 10% of the entire pore volume, especially preferably, 15 to 40%, and the pore volumes composed of pores having pore diameters in the range of from 1.0 to less than 10.0 μm and pores having pore diameters in the range from 0.1 to 100 μm are not less than 10% of the entire pore volume respectively, especially preferably, 15 to 65% respectively. It was found that when these conditions are satisfied, both of the activity and the selectivity of the above catalyst are enhanced that is, a pore having a smaller pore diameter, e.g., less than 1.0 μm, has a larger contribution toward the surface area and pore volume than pores having a larger pore diameters, e.g. larger than 0.1 μm. However, in the pores having a contribution toward the activity and selectivity to the effective reaction product, the mere larger proportion of the smaller pores is not sufficient. And if there is not a distribution in which pores are also distributed in two ranges of from 1.0 to less than 10.0 μm and from 10.0 to 100 μm, it is not possible to obtain enhancement of the performance.

On the basis of the above finding, the present inventors diligently continued the studies and consequently found that the use of a centrifugal flow coating apparatus in shaping of an unfired catalyst powder not formed into particles can give catalysts which are excellent in reproducibility and exhibit excellent catalyst performance.

In usual formation methods of catalysts, a rolling particle-forming method, marmerizer-forming method, fluidized bed particle-forming method, etc., are used for the preparation of spherical shapes, and an extrusion method, tablet-forming method, etc., are used for cylindrical shapes. However, in the case of using these formation methods, it is difficult in many cases to form catalysts without degrading the catalyst performance, the performance frequently varies widely and the reproducibility is often poor. In contrast thereto, in the use of a centrifugal flow coating apparatus according to this invention, the apparatus is simply operated and gives good reproducibility and it is possible to prepare spherical or particulate catalysts. Further, the formation by a centrifugal flow coating apparatus also has advantages that catalysts having a narrow distribution of particle size can be obtained and that, since said catalysts are particulate or spherical, the catalysts have high mechanical strength, little pressure loss and high resistance to friction and are easy to fill in or take out from a reaction apparatus.

Meanwhile, the use of a centrifugal flow coating device is known as one method of forming particles from powder material. For example, Japanese Patent Publication No. 10878/1971 discloses said use with regard to a case where pharmaceutical compositions are sugar-coated. Japanese Pat. Publication No. 17292/1977 also discloses it with regard to a case where particulate cores are coated with a catalyst and/or carriers.

In this invention, this method is applied to the preparation of the above-mentioned oxide catalyst. According to the process of this invention, it is possible to easily obtain a spherical or particulate catalyst having the aforespecified surface area, pore volume and pore diameter distribution and having high physical strength by only using water as a binder or by optionally using, in combination therewith, a substance which imparts the catalyst with pores by combustion or volatilization at the time of firing. The catalyst of this invention can be produced, for example, by charging an unfired catalyst material powder composition into a centrifugal flow coating apparatus to form particles with blowing heated air thereinto and spraying a binder such as water, taking out particles grown to the desired size in batchtype operation or in successive operation, then drying the particles as necessary and thereafter firing them at a temperature of 200 to 500° C., preferably 300° to 450° C.

The catalyst of this invention can be used directly as such, or by diluting it with an inert carrier or in the state in which the catalyst is held in said carrier. In the formation of the particles, it is preferable to use, as a core, granules obtained by preforming a catalyst per se to a size more than 10 times larger than the particle size of the material powder. Naturally, an inert carrier can be also used as this core. Examples of the inert carrier include silicon carbide, silica, alpha-alumina and others known as a refractory material. With regard to a coating catalyst powder to grow a particle diameter, it is preferable to preadjust the powder to not more than 100 mesh. In order to prepare a catalyst having the surface area, pore volume and pore diameter distribution specified by this invention with good reproducibility, for example, a polyvinyl alcohol, stearic acid, etc., may be added to the catalyst material powder composition at the time of preparing said composition or at the time of shaping. As a binder of the powder, it is also possible to use water, ammonium nitrate, graphite, starch, etc, and organic solvents such as alcohol, acetone, etc., can be used as well.

The chemical composition of the catalyst of this invention is known in itself and is represented by the following general formula

$Mo_{(a)}V_{(b)}A_{(c)}B_{(d)}C_{(e)}D_{(f)}O_{(x)}$ (wherein Mo represents molybdenum, V represents vanadium, A represents at least one element selected from the group consisting of tungsten and niobium, B represents at least one element selected from the group consisting of iron, copper, bismuth, chromium, antimony and thallium C represents at least one element selected from the group consisting of alkali metals and alkaline earth metals, D represents at least one element selected from the group consisting of silicon, aluminum and titanium, and 0 represents oxygen; and further, a, b, c, d, e, f and x represent atomic ratios of Mo, V, A, B, C, D, and 0 respectively, and when a=12, then b=2 to 14, c=0 to 12, d=0 to 6, e=0 to 6 and f=0 to 30 and x is a numerical value determined depending upon the oxidation states of the other elements).

A catalytic gas phase oxidation reaction of this invention is carried out by introducing a material gas composed of 1 to 10% by volume of acrolein, 1 to 15% by volume of molecular oxygen, 5 to 60% by volume of water vapor and 20 to 80% by volume of an inert gas (e.g., a mixed gas consisting of nitrogen, carbonic acid gas, saturated hydrocarbon gas, etc. onto the catalyst at a temperature in the range of from 150° to 400 ° C. at a pressure of atmospheric pressure to 10 atm and at a space velocity of 500 to 20,000hr $^{-1}$(STP) In addition, as a material gas, an acrolein-containing gas obtained by catalytic reaction of propylene may be also used directly.

The following Examples and Comparative Examples illustrate this invention more in detail. However, this invention shall not be limited to these Examples. In this invention, the conversion ratio and the yield in a single flow are respectively defined as follows.

Conversion ratio (%) =

$$\frac{\text{Number of moles of reacted acrolein}}{\text{Number of moles of charged acrolein}} \times 100$$

Yield in a single flow (%) =

$$\frac{\text{Number of moles of produced acrylic acid}}{\text{Number of moles of charged acrolein}} \times 100$$

EXAMPLE I (Preparation of suspension of catalyst material)

While 50 liters of water was stirred under heat, dissolved therein were 1,560 g of ammonium paratungstate, 1,290 g of ammonium metavanadate, 5,070 g of ammonium molybdate and 180 g of ammonium dichromate to prepare an aqueous solution. Separately, 1,290 g of copper nitrate was dissolved in 3.0 liters of water to prepare another aqueous solution. These two solutions were mixed, and the mixture solution was heated and stirred to give a suspension. (The suspension is referred to as a suspension-A.)

EXAMPLE I-1-1

(Preparation of a catalyst by a centrifugal flow coating method)

A part of the suspension A was evaporated to dry solidness with stirring under heat. Then the resultant solid in the block state was dried in a drier at 120° C. for 5 hours, and milled to about 100 mesh to give a powder. Alpha-alumina particles having an average diameter of 1 mm was first charged to a centrifugal flow coating apparatus. Then the above powder was charged thereto together with distilled water as a binder with blowing heated air at 90° C., and spherical particles having an average diameter of 5 mm were formed. The spherical particles obtained as above were fired at a temperature of 400° C. for 5 hours. The compositional ratio of the elements except oxygen in the resultant catalyst oxide was $Mo_{(12)}V_{(4.6)}Cu_{(2.2)}Cr_{(0.6)}W_{(2.4)}$. This catalyst is referred to as a catalyst (I-1-1).

EXAMPLE I-1-2

(Preparation of a catalyst by a centrifugal flow coating method)

Example I-1-1 was repeated except that 40 wt. % ammonium nitrate aqueous solution was used as a binder in place of water, and a catalyst (I-1-2) was obtained.

EXAMPLES I-2-1 and I-2-2

(Preparation of catalysts by tablet-forming method)

A part of the suspension-A was evaporated to dry solidness with stirring under heat. Then the resultant solid in the block state was dried in a drier under air current at 120° C. for 5 hours, and the dried block was milled to not more than 100 mesh to give a powder. 2% by weight of a carbon powder was added to the powder, and the resultant mixture was formed into tablets having a diameter of 5 mm and height of 5 mm. The tablets were fired at 400° C. for 5 hours to prepare a catalyst (I-2-1). The same procedure was repeated to prepare another catalyst (I-2-2).

EXAMPLES I-3-1 and I-3-2

(Preparation of a catalyst by extrusion method)

A part of the suspension-A was concentrated by evaporation until it could be extruded, and extruded so as to form extrudates having a diameter of 5 mm and length of 5 mm. The extrudates were fired at 400° C. for 5 hours to prepare a catalyst (I-3-1). The same procedure was repeated to prepare another catalyst (I-3-2).

EXAMPLES I-4

(Preparation of a catalyst by marmerizer-forming method)

A part of the suspension-A was subjected to concentrating heat treatment by external heat to concentrate it until it could be extruded. The concentrate was extrusion-molded to form extrudates having a diameter of 6 mm and length of 4 to 7 mm. Then the extrudates were subjected to a marmerizer to form 3 mm×5 mm spheroids. The spheroids were fired at 400° C. for 5 hours to prepare a catalyst (I-4).

EXAMPLE I-5

(Preparation of a catalyst by rolling particle-forming method)

A part of the suspension-A was evaporated to dry solidness with stirring under heat. Then the resultant solid in the block state was dried in a drier at 120° C. for 5 hours, and the dried block was milled to about 100 mesh to obtain a powder. Alpha-alumina particles having an average diameter of 1 mm were charged first into a rolling particle-forming machine. And then the above powder was charged thereinto, and heated air at 80° C. and distilled water as a binder were used to form spheres having an average diameter of 5 mm. The spheres were fired at 400° C. for 5 hours to prepare a catalyst (I-5).

EXAMPLE I-6

(Preparation of a catalyst by pill-forming method)

A part of the suspension-A was subjected to concentrating heat treatment by externally heating to obtain a soil-like substance, 50% by weight of which was dissipated when it was fired at 400° C. The soil-like substance was formed by a pill-forming machine into spheres having an average diameter of 5 mm. The spheres were fired at 400° C. for 5 hours to prepare a catalyst (I-6).

[Reaction Test]

The activity test on each of the above catalysts I-1 to I-6 was carried out in the following procedure.

1,000 ml of the catalyst was charged to a steel reaction tube having an internal diameter of 25.4 mm, and a mixture gas obtained by catalytic gas phase oxidation of industrial-use propylene (having a purity of not less than 95%) in the presence of a catalyst of a molybdenum/cobalt/tungsten oxide type was introduced thereinto to carry out the reaction at a reaction temperature of 200° to 250° C. and at a space velocity of 3,000 $hr^{-1}$. The average composition of the mixture gas for the reaction was as follows.

| | |
|---|---|
| Acrolein | 5.64% by volume |
| Propylene + propane | 0.65% by volume |
| Acrylic acid + acetic acid | 0.74% by volume |
| Nitrogen | 70.03% by volume |
| Water vapor | 17.22% by volume |
| Oxygen | 4.75% by volume |
| Others | 0.97% by volume |

EXAMPLE I-1-3

An 8,000 hour-successive reaction test was carried out by the use of the catalyst of Example I-1-1. The procedure for the reaction test was the same as in Example I. The temperature in the beginning of the reaction was 200° C., however, it was sufficient to elevate the temperature by 5° C. during the period of time of 8,000 hours. The reaction results at the reaction temperature of 205° C. were that the acrolein conversion ratio was 99.6% and the yield of acrylic acid in a single flow was 97.0%.

EXAMPLE I-7

(Preparation of a catalyst on a carrier)

A part of the suspension-A was charged into an evaporator on a hot water bath, and added thereto was a particulate alpha-alumina carrier having a specific surface area of 1 m²/g, a porosity of 42%, a pore distribution, 92% of which was made by pores having diameters of 75 to 250 microns, and diameters of 3 to 5 mm. The mixture was evaporated to dry solidness with stirring, and then fired at 400° C. for 5 hours to prepare a catalyst (I-7). The reaction test was carried out in the same way as in Examples I-1 to I-6.

Table 1 shows physical properties and activities measured with regard to the catalysts I-1 to I-7.

series, and the reproducibility in the same forming method was examined by comparing the performances. In the same forming method, catalysts of the four batches were prepared independently of one another in the same procedure and under the same conditions. The performance tests were carried out according to the procedure of Examples I-1 to I-7 series except that the test in Example II-1 was carried out according to Example I-1-1.

The results are shown in Table 2.

As is clear in Table 2, catalysts resulting from formation by centrifugal coating method have a smaller variation in values of physical property and high activity in catalyst performance, and it is seen on the basis of the smaller variation that the catalysts were prepared with

TABLE 1

| Example | Forming method | Surface area m²/g | Pore volume cc/g | Pore distribution A*1 | Pore distribution B*2 | Pore distribution C*3 | Reaction temperature (°C.) | Acrolein conversion ratio | Yield of acrylic acid in a single flow |
|---|---|---|---|---|---|---|---|---|---|
| I-1-1 | Centrifugal flow coating method | 4.7 | 0.250 | 22 | 21 | 55 | 210 | 99.8 | 97.1 |
| I-1-2 | " | 4.8 | 0.247 | 23 | 22 | 54 | 200 | 99.6 | 97.5 |
| I-2-1 | Tablet-forming method | 2.7 | 0.150 | — | 25 | 70 | 210 | 90.6 | 75.2 |
| I-2-2 | " | 2.0 | 0.110 | — | 21 | 74 | 210 | 85.3 | 72.5 |
| I-3-1 | Extrusion method | 3.5 | 0.170 | — | 30 | 68 | 210 | 92.4 | 84.1 |
| I-3-2 | " | 3.2 | 0.163 | — | 35 | 60 | 210 | 89.8 | 82.6 |
| I-4 | Marmerizer-forming method | 3.7 | 0.160 | — | 31 | 65 | 210 | 90.1 | 83.3 |
| I-5 | Rolling particle forming method | 4.1 | 0.210 | 6 | 30 | 60 | 210 | 94.8 | 90.1 |
| I-6 | Pill-forming method | 4.7 | 0.220 | 8 | 28 | 62 | 210 | 93.2 | 88.5 |
| I-7 | Carrier added-forming method | 1.50 | 0.180 | — | 40 | 55 | 210 | 87.4 | 87.0 |

*¹Ratio (%) of pore volume consisting of pores having diameters in the range of from 10 to 100 μm to the entire pore volume. (The asterisk in the other Tables means the same.)
*²Ratio (%) of pore volume consisting of pores having diameters in the range of from 1 to less than 10 μm to the entire pore volume. (The asterisk in the other Tables means the same.)
*³Ratio (%) of pore volume consisting of pores having diameters in the range of from 0.1 to less than 1 μm to the entire pore volume. (The asterisk in the other Tables means the same.)

EXAMPLE II (Preparation of a catalyst and test on reproducibility thereof)

A suspension was prepared in the same way as in Example 1 and divided into four equal portions for four batches. From these four batches, powders or clay-like substances were prepared as materials suitable for various forming methods. The materials were formed into catalysts in the same way as in Examples I-1 to I-7 good reproducibility. On the other hand, it is further seen that the other formation methods in some batches give catalysts which do not have the surface area, pore volume and pore distribution specified by this invention, although the catalysts were prepared under the same conditions, and that, as method for obtaining catalysts having good performance with good reproducibility, these other forming methods are inferior to the centrifugal flow coating method.

TABLE 2

| Example | Forming method | Batch No. | Surface area m²/g | Pore volume cc/g | Pore distribution A*1 | Pore distribution B*2 | Pore distribution C*3 | Reaction temperature (°C.) | Acrolein conversion ratio | Yield of acrylic acid in a single flow |
|---|---|---|---|---|---|---|---|---|---|---|
| II-1 | Centrifugal flow coating method | 1 | 4.7 | 0.246 | 23 | 23 | 52 | 210 | 99.6 | 97.4 |
|  | " | 2 | 4.8 | 0.252 | 23 | 20 | 54 | 210 | 99.7 | 97.3 |
|  | " | 3 | 4.9 | 0.251 | 21 | 21 | 56 | 210 | 99.6 | 97.5 |
|  | " | 4 | 4.6 | 0.251 | 24 | 22 | 52 | 210 | 99.5 | 97.4 |
| II-2 | Tablet-forming method | 1 | 2.5 | 0.170 | — | 20 | 77 | 210 | 89.8 | 76.7 |
|  | " | 2 | 2.0 | 0.160 | — | 23 | 76 | 210 | 87.1 | 74.9 |
|  | " | 3 | 2.9 | 0.200 | — | 29 | 68 | 210 | 92.0 | 77.4 |
|  | " | 4 | 2.3 | 0.171 | — | 27 | 72 | 210 | 90.3 | 75.5 |
| II-3 | Extrusion method | 1 | 3.0 | 0.185 | — | 31 | 66 | 210 | 90.7 | 83.4 |
|  | " | 2 | 3.2 | 0.190 | — | 30 | 65 | 210 | 89.8 | 84.4 |
|  | " | 3 | 2.7 | 0.153 | — | 25 | 74 | 210 | 86.1 | 80.9 |
|  | " | 4 | 3.4 | 0.216 | — | 42 | 56 | 210 | 95.2 | 87.1 |
| II-4 | Marmerizer-forming method | 1 | 3.3 | 0.186 | — | 35 | 61 | 210 | 91.3 | 85.8 |
|  | " | 2 | 3.5 | 0.211 | — | 32 | 67 | 210 | 89.1 | 84.6 |
|  | " | 3 | 2.6 | 0.200 | — | 23 | 73 | 210 | 85.7 | 79.7 |
|  | " | 4 | 2.9 | 0.217 | — | 25 | 74 | 210 | 87.3 | 81.7 |
| II-5 | Rolling particle forming method | 1 | 4.8 | 0.230 | 6 | 31 | 60 | 210 | 95.2 | 90.7 |
|  | " | 2 | 3.9 | 0.210 | 4 | 32 | 62 | 210 | 96.0 | 91.5 |
|  | " | 3 | 4.3 | 0.189 | 3 | 25 | 71 | 210 | 97.3 | 92.0 |
|  | " | 4 | 4.4 | 0.214 | 7 | 42 | 47 | 210 | 94.7 | 90.8 |

TABLE 2-continued

| Example | Forming method | Batch No. | Surface area m²/g | Pore volume cc/g | Pore distribution A[*1] | B[*2] | C[*3] | Reaction temperature (°C.) | Acrolein conversion ratio | Yield of acrylic acid in a single flow |
|---|---|---|---|---|---|---|---|---|---|---|
| II-6 | Pill-forming method | 1 | 4.8 | 0.220 | 3 | 25 | 71 | 210 | 92.6 | 88.9 |
|  | " | 2 | 5.1 | 0.217 | 4 | 27 | 65 | 210 | 94.7 | 90.9 |
|  | " | 3 | 4.0 | 0.169 | 2 | 23 | 74 | 210 | 90.5 | 87.8 |
|  | " | 4 | 4.6 | 0.182 | 7 | 31 | 61 | 210 | 91.7 | 85.3 |
| II-7 | Carrier added-forming method | 1 | 1.7 | 0.153 | — | 41 | 58 | 210 | 86.2 | 84.5 |
|  | " | 2 | 1.9 | 0.193 | — | 57 | 40 | 210 | 93.1 | 89.4 |
|  | " | 3 | 1.2 | 0.167 | — | 40 | 59 | 210 | 87.3 | 85.9 |
|  | " | 4 | 1.6 | 0.148 | — | 51 | 47 | 210 | 85.1 | 82.8 |

EXAMPLE III (Preparation of material suspension for catalyst)

While 6.0 liters of water was heated with stirring, 234.0 g of ammonium metavanadate and 1,059.4 g of ammonium molybdate were dissolved in the water to prepare an aqueous solution. Separately, 241.6 g of copper nitrate and 40.4 g of ferric nitrate were dissolved in water to prepare another aqueous solution. These two aqueous solution were mixed. And further, added to the resulting solution was 134 ml of 20% by weight of $SiO_2$-containing silica sol as a carrier to form a suspension. (The suspension is referred to as suspension-B.)

EXAMPLE III-1

(Preparation of a catalyst by centrifugal flow coating method)

A part of the suspension-B was treated in the same way as in Example I-1-1 to prepare a catalyst. However, the firing was carried out at 400° C. for 6 hours. The compositional ratio of the elements except oxygen in the resultant catalyst oxide was $Mo_{(12)}V_{(4)}Cu_{(2)}Fe_{(0.2)}Si_{(1.0)}$.

EXAMPLES III-2-1 and III-2-2

(Preparation of catalysts by tablet-forming method)

A part of the suspension-B was treated in the same way as in Example I-2 to prepare catalysts. However, the firing was carried out at 400° C. for 6 hours.

[Reaction test]

By the use of the catalysts of Examples III-1 to III-2, the reactions were carried out in the same way as in Example I, except that the reaction temperature was set at 230° C.

EXAMPLE IV (Preparation of material suspension for catalyst)

Ammonium molybdate (1,596 g) was dissolved in 12 liters of water under heat. 220.8 g of ammonium metavanadate, 1,126.5 g of niobium hydroxide, 162 g of ferrous oxalate, 88.5 g of cuprous chloride and 45 g of potassium nitrate were consecutively added to the above solution with fully stirring. After the mixture was heated with stirring, 678 g of an $SiO_2$ powder was added to prepare a suspension. (This suspension is referred to as a suspension-C.)

Example IV-1

(Preparation of a catalyst by centrifugal flow coating method)

A part of the suspension-C was treated in the same way as in Example I-1-1 to prepare a catalyst except that the firing was carried out at 420° C. for 5 hours. The compositional ratio of the elements except oxygen in the resultant catalyst oxide was $Mo_{(12)}V_{(2.5)}Nb_{(8.4)}Cu_{(1.2)}Fe_{(1.2)}K_{(0.6)}Si_{(15)}$.

EXAMPLES IV-2-1 and IV-2-2

(Preparation of catalysts by extrusion method)

A part of the suspension-C was treated in the same way as in Example I-3 to prepare catalysts. However, the firing was carried out at 420° C. for 5 hours.

[Reaction test]

By the use of the catalysts of Examples IV-1 to IV-2, the reactions were carried out in the same way as in Example I, except that the reaction temperature was set at 240° C.

EXAMPLE V (Preparation of material suspension for catalyst)

A suspension was obtained in the same way as in Example I. There were used antimony pentoxide as an antimony source, a nitrate as a magnesium source and an oxide as an aluminum source. (This suspension is referred to as a suspension-D.)

EXAMPLE V-1

(Preparation of a catalyst by centrifugal flow coating method)

A part of the suspension-D was treated in the same way as in Example I-1-1 to prepare a catalyst. The compositional ratio of the elements except oxygen in the resultant catalyst oxide was $Mo_{(12)}V_{(4.0)}Sb_{(0.5)}Mg_{(2.0)}Al_{(5.0)}$.

EXAMPLES V-2-1 and V-2-2

(Preparation of catalysts by marmerizer-forming method)

A part of the suspension-D was treated in the same way as in Example I-4 to prepare catalysts.

[Reaction test]

By the use of the catalysts of Examples V-1 to V-2, the reactions were carried out in the same way as in Example I, except that the reaction temperature was set at 240° C.

EXAMPLE VI (Preparation of material suspension for catalyst)

A suspension was obtained in the same way as in Example I. As a cesium source and strontium source, nitrates were used, and as a titanium source, an oxide was used. (This suspension is referred to as a suspension-E.)

EXAMPLE VI-1

(Preparation of a catalyst by centrifugal flow coating method)

A part of the suspension-E was treated in the same way as in Example I-1-1 to prepare a catalyst. The compositional ratio of the elements except oxygen in the resultant catalyst oxide was $Mo_{(12)}V_{(4)}W_{(2.0)}Cu_{(2.0)}Sr_{(2.0)}Ti_{(10)}$.

EXAMPLES VI-2-1 and VI-2-2

(Preparation of a catalyst by rolling particle-forming method)

A part of the suspension-E was formed into catalysts according to Example I-5.

[Reaction test]

By the use of the catalysts of Examples VI-1 to VI-2, the reactions were carried out in the same way as in Example I, except that the reaction temperature was set at 220° C.

EXAMPLE VII (Preparation of material suspension for catalyst)

A suspension was obtained in the same way as in Example I. Additionally used were ferric nitrate as an iron source, sodium nitrate as a sodium source and an oxide as an aluminum source. (This suspension is referred to as a suspension-F.)

EXAMPLE VII-1

(Preparation of a catalyst by centrifugal flow coating method)

A part of the suspension-F was treated in the same way as in Example I-1-1 to prepare a catalyst. The compositional ratio of the elements except oxygen in the resultant catalyst oxide was $Mo_{(12)}V_{(8.0)}W_{(4.0)}Cu_{(1.0)}Fe_{(1.0)}Na_{(0.5)}Al_{(5.0)}$.

EXAMPLES VII-2-1 AND VII-2-2

(Preparation of a catalyst by pill-forming method)

A part of the suspension-F was formed into catalysts according to Example I-6.

[Reaction test]

By the use of the catalysts of Examples VII-1 to VII-2, the reactions were carried out in the same way as in Example I, except that the reaction temperature was set at 210° C.

EXAMPLE VIII (Preparation of material suspension for catalyst)

A suspension was obtained in the same way as in Example I. In addition, there were used nitrates as bismuth and rubidium sources and silica gel as a silicon source. (This suspension is referred to as a suspension-G).

EXAMPLE VIII-1

(Preparation of a catalyst by centrifugal flow coating method)

A part of the suspension-G was treated in the same way as in Example I-1-1 to prepare a catalyst. The compositional ratio of the elements except oxygen in the resultant catalyst oxide was $Mo_{(12)}V_{(8.0)}W_{(4.0)}Cu_{(1.0)}Bi_{(1.0)}Rb_{(0.05)}Si_{(5.0)}$.

EXAMPLES VIII-2-1 AND VIII-2-2

(Preparation of a catalyst by carrier-added forming method)

A part of the suspension-G was formed into catalysts according to Example I-7.

[Reaction test]

By the use of the catalysts of Examples VIII-1 to VIII-2, the reactions were carried out in the same way as in Example I.

EXAMPLE IX (Preparation of material suspension for catalyst)

A suspension was obtained in the same way as in Example I. In addition, there were used nitrates as bismuth and cesium sources and silica gel as a silicon source. (This suspension is referred to as a suspension-H).

EXAMPLE IX-1

(Preparation of a catalyst by centrifugal flow coating method)

A part of the suspension-H was treated in the same way as in Example I-1-1 to prepare a catalyst. The compositional ratio of the elements except oxygen in the resultant catalyst oxide was $Mo_{(12)}V_{(8.0)}W_{(1.0)}Bi_{(1.0)}Cs_{(0.05)}Si_{(5.0)}$.

EXAMPLES IX-2-1 AND IX-2-2

(Preparation of a catalyst by tablet-forming method)

A part of the suspension-H was formed into catalysts according to Example I-2.

[Reaction test]

By the use of the catalysts of Examples IX-1 to IX-2, the reactions were carried out in the same way as in Example I.

The results of the above Examples III to IX are summarized in Table 3.

TABLE 3

| Example | Forming method | Surface area m²/g | Pore volume cc/g | Pore distribution A*1 | B*2 | C*3 | Reaction temperature (°C.) | Acrolein conversion ratio | Yield of acrylic acid in a single flow |
|---|---|---|---|---|---|---|---|---|---|
| III-1 | Centrifugal flow coating method | 5.0 | 0.283 | 21 | 30 | 48 | 230 | 96.8 | 92.9 |
| III-2-1 | Tablet-forming method | 3.1 | 0.216 | — | 25 | 70 | 230 | 92.0 | 84.6 |

TABLE 3-continued

| Example | Forming method | Surface area m²/g | Pore volume cc/g | Pore distribution A*1 | B*2 | C*3 | Reaction temperature (°C.) | Acrolein conversion ratio | Yield of acrylic acid in a single flow |
|---|---|---|---|---|---|---|---|---|---|
| III-2-2 | " | 2.2 | 0.179 | — | 17 | 82 | 230 | 88.5 | 82.3 |
| IV-1 | Centrifugal flow coating method | 6.3 | 0.324 | 18 | 33 | 48 | 240 | 94.3 | 90.5 |
| IV-2-1 | Extrusion method | 4.1 | 0.261 | — | 42 | 57 | 240 | 91.7 | 85.5 |
| IV-2-2 | " | 2.9 | 0.215 | — | 30 | 69 | 240 | 88.4 | 80.6 |
| V-1 | Centrifugal flow coating method | 4.1 | 0.305 | 16 | 32 | 49 | 240 | 98.7 | 89.8 |
| V-2-1 | Marmerizer-forming method | 3.9 | 0.213 | — | 31 | 66 | 240 | 92.5 | 81.4 |
| V-2-2 | " | 2.6 | 0.192 | — | 46 | 53 | 240 | 89.8 | 82.6 |
| VI-1 | Centrifugal flow coating method | 4.2 | 0.295 | 19 | 27 | 50 | 220 | 99.6 | 95.6 |
| VI-2-1 | Rolling particle forming method | 4.7 | 0.281 | 7 | 40 | 50 | 220 | 95.1 | 91.3 |
| VI-2-2 | " | 3.6 | 0.325 | 3 | 23 | 71 | 220 | 92.6 | 89.8 |
| VII-1 | Centrifugal flow coating method | 5.6 | 0.371 | 23 | 34 | 40 | 220 | 99.1 | 95.5 |
| VII-2-1 | Pill-forming method | 4.1 | 0.257 | 3 | 21 | 71 | 220 | 93.4 | 89.7 |
| VII-2-2 | " | 4.9 | 0.326 | 9 | 18 | 69 | 220 | 96.7 | 90.9 |
| VIII-1 | Centrifugal flow coating method | 4.3 | 0.310 | 35 | 20 | 41 | 210 | 97.8 | 94.9 |
| VIII-2-1 | Carrier added-forming method | 1.2 | 0.126 | — | 44 | 51 | 210 | 86.9 | 82.6 |
| VIII-2-2 | " | 1.8 | 0.192 | — | 50 | 48 | 210 | 89.3 | 83.9 |
| IX-1 | Centrifugal flow coating method | 4.3 | 0.256 | 21 | 29 | 49 | 210 | 97.9 | 94.0 |
| IX-2-1 | Tablet-forming method | 2.1 | 0.169 | — | 21 | 76 | 210 | 91.6 | 87.9 |
| IX-2-2 | " | 3.3 | 0.217 | — | 30 | 68 | 210 | 94.3 | 88.9 |

EXAMPLE X-1

(Preparation of catalyst by a centrifugal flow coating method)

Example I-1-1 was repeated except that alpha-alumina particle having an average diameter of 3 mm was first charged to a centrifugal flow coating apparatus as a core in place of alpha-alumina particle having an average diameter of 1 mm.

EXAMPLE X-2

Example X-1 was repeated except that alpha-alumina particle having an average diameter of 5 mm was first charged as a core.

[Reaction test]

By the use of the catalysts of Examples X-1 to X-2, the reaction was carried out in the same way as in Example I. The reaction results at the reaction temperature of 210° C. were that the acrolein conversion ratio was 99 6% and the yield of acrylic acid in a single flow was 97.2% for Example X-1 and the acrolein conversion ratio was 99.4% and the yield of acrylic acid in a single flow was 97.3% for Example X-2.

As for Example X-1, surface area was 4.0 m²/g, and pore volume was 0.237 cc/g, and the ratio of pore volume consisting of pores having diameters in the range of from 10 to 100 μm, from 1 to less than 10 μm, from 0.1 to less than 1 μm to the entire pore volume were 22%, 20% and 48% respectively.

As for Example X-2, surface area was 2.5 m²/g, and pore volume was 0.185 cc/g, and the ratio of pore volume consisting of pores having diameters in the range of from 10 to 100 μm, from 1 to less than 10 μm, from 0.1 to less than 1 μm to the entire pore volume were 22%, 21% and 55% respectively.

What we claim is:

1. A catalyst for use in the production of acrylic acid by catalytic gas phase oxidation of acrolein, comprising active substances represented by general formula wherein Mo represents molybdenum, V represents vanadium, A represents at least one element selected from the group consisting of tungsten and niobium, B represents at least one element selected from the group consisting of iron, copper, bismuth, chromium, antimony and thallium, C represents at least one element selected from the group consisting of alkali metals and alkaline earth metals, D represents at least one element selected from the group consisting of silicon, aluminum and titanium, and O represents oxygen; and further, a, b, c, d, e, f and x represents atomic ratios of Mo, V, A, B, C, D, and O respectively, and when a=12, then b=2 to 14, c=0 to 12, d? 0 to 6, e? 0 to 6 and f? 0 to 30 and x is a numerical value determined depending upon the oxidation states of the other elements, and said catalyst being prepared by charging an unfired catalyst material powder into a centrifugal flow coating apparatus to form particles, and firing the particles, wherein said particles are characterized by having a specific surface area of 0.50 to 15.0 m²/g, a pore volume of 0.10 to 0.90 cc/g and a pore diameter distribution in which the pore diameters are distributed concentratedly in each of the ranges of from 0.1 to less than 1.0 μm, from 1.0 to less than 10.0 μm and from 10.0 to 100 μm.

2. A catalyst according to claim 1 wherein the pore volume composed of pores having pore diameters in the range of from 0.1 to less than 1.0 μm, the pore volume composed of pores having pore diameters in the range of from 1.0 to less than 10.0 μm and the pore volume composed of pores having pore diameters in the range of from 10 to 100 μm are each respectively at least 10% based on the entire pore volume.

3. A catalyst according to claim 1 wherein the pore volume composed of pores having pore diameters in the range of from 10 to less than 100 μm, the pore volume composed of pores having pore diameters in the range of from 1.0 to less than 10.0 μm and the pore volume composed of pores having pore diameters in the range of from 0.1 to 1.0 μm are respectively 15 to 40%, 15 to 65% and 15 to 65% based on the entire pore volume.

4. In a process for preparation, with good reproducibility, of a catalyst which is used in the production of acrylic acid by catalytic gas phase oxidation of acrolein and which comprises active substances represented by the general formula $$Mo_{(a)}V_{(b)}A_{(c)}B_{(d)}C_{(e)}D_{(f)}O_{(x)}$$

wherein Mo represents molybdenum, V represents vanadium, A represents at least one element selected from the group consisting of tungsten and niobium, B represents at least one element selected from the group consisting of iron, copper, bismuth, chromium, antimony and thallium, C represents at least one element selected from the group consisting of alkali metals and alkaline earth metals, D represents at least one element selected from the group consisting of silicon, aluminum and titanium, and O represents oxygen; and further, a, b, c, d, e, f and x represent atomic ratios of Mo, V, A, B, C, D, and O, respectively, and when $a=12$, then $b=2$ to 14, $c=0$ to 12, $d=0$ to 6, $e=0$ to 6 and $f=0$ to 30 and x is a numerical value determined depending upon the oxidation states of the other elements; the improvement comprising charging an unfired catalyst material powder composition into a centrifugal flow coating apparatus to form particles having an average diameter of 2 to 10 mm, and then firing the particles thereby to obtain the catalyst having a specific surface area of 0.50 to 15.0 $m^2/g$, a pore volume of 0.10 to 0.90 cc/g and a pore diameter distribution in which the pore diameters are distributed concentratedly in each of the ranges of from 0.1 to less than 1.0 $\mu m$, from 1.0 to less than 10.0 $\mu m$ and from 10.0 to 100 $\mu m$.

5. A process according to claim 4 for the preparation of a catalyst in which the pore volume composed of pores having pore diameters in the range of from 0.1 to less than 1.0 $\mu m$, the pore volume composed of pores having pore diameters in the range of from 1.0 to less than 10.0 $\mu m$ and the pore volume composed of pores having pore diameters in the range of from 10 to 100 $\mu m$ are each respectively at least 10% based on the entire pore volume.

6. A process according to claim 4 for the preparation of a catalyst in which the pore volume composed of pores having pore diameters in the range of from 10 to less than 100 $\mu m$, the pore volume composed of pores having pore diameters in the range of from 1.0 to less than 10.0 $\mu m$ and the pore volume composed of pores having pore diameters in the range of from 0.1 to 1.0 $\mu m$ are respectively 15 to 40%, 15 to 65% and 15 to 65% based on the entire pore volume.

* * * * *

UNITED STATES PATENT AND TRADEMARK OFFICE
CERTIFICATE OF CORRECTION

PATENT NO. : 4,892,856
DATED : January 9, 1990
INVENTOR(S) : TATSUYA KAWAJIRI ET AL.

It is certified that error appears in the above-identified patent and that said Letters Patent is hereby corrected as shown below:

Claim 1, between lines 3 and 4, insert the following formula:
 --$Mo_{(a)}V_{(b)}A^{A}_{(c)}B^{B}_{(d)}C^{C}_{(e)}D^{D}_{(f)}O_{(x)}$--;

line 17 of the claim, "d? 0 to 6, e? 0 to 6 and f? 0 to 30" should read as follows:
--d=0 to 6, e=0 to 6 and f=0 to 30--.

Claim 4, lines 1 and 2, "reproductibility" should read
--reproducibility--.

Signed and Sealed this

Fifth Day of March, 1991

*Attest:*

HARRY F. MANBECK, JR.

*Attesting Officer*  *Commissioner of Patents and Trademarks*